United States Patent [19]

Tovar et al.

[11] Patent Number: 4,795,450

[45] Date of Patent: Jan. 3, 1989

[54] NON-SPATTERING HYGIENIC NAPKIN FOR MEN

[76] Inventors: Juan R. Tovar; Maria Tovar, both of 405 Broadway, Bayonne, N.J. 07002

[21] Appl. No.: 77,745

[22] Filed: Jul. 27, 1987

[51] Int. Cl.$^4$ ............................................. A61F 5/44
[52] U.S. Cl. ............................ 604/349; 128/760; 128/DIG. 15; 604/317; 604/352; 604/353
[58] Field of Search ............... 128/349, 760, 762, 767; 604/327, 349, 318, 351, 353; 4/144.1–144.4

[56] References Cited

U.S. PATENT DOCUMENTS

| | | | |
|---|---|---|---|
| 2,873,740 | 2/1959 | Wainwright | 604/349 X |
| 2,891,546 | 6/1959 | Galloway | 604/353 |
| 2,896,788 | 7/1959 | Hoffberger | 604/317 X |
| 3,030,958 | 4/1962 | Levin | 604/347 |
| 4,064,880 | 12/1977 | Logan | 128/132 R |
| 4,378,018 | 3/1983 | Alexander et al. | 128/760 X |
| 4,576,599 | 3/1986 | Lipner | 604/352 |
| 4,590,931 | 5/1986 | Kidwell, Jr. | 128/DIG. 15 |
| 4,601,716 | 7/1986 | Smith | 604/353 X |
| 4,668,229 | 5/1987 | Fago et al. | 604/349 X |

*Primary Examiner*—Larry Jones
*Attorney, Agent, or Firm*—Norman B. Rainer

[57] ABSTRACT

A disposable shaped absorbent paper napkin is provided for hygienic use by men. The napkin is intended to accommodate the penis and absorb residual urine in the urethra tube following urination.

2 Claims, 2 Drawing Sheets

NON-SPATTERING HYGIENIC NAPKIN FOR MEN

BACKGROUND OF THE INVENTION

This invention concerns a paper product, and more particularly relates to a disposable shaped absorbent paper product useful in a specialized sanitary application.

In the anatomy of the male human, urine which collects in the bladder is excreted during the act of urination by passage through the urethra tube, past the prostate gland which interacts in valve-like manner with the uretha tube, ultimately exiting from the glans penis. However, several drops of residual urine may remain within the urethra in route to the glans penis. Greater amounts of such residual urine occur with disorders of the prostate gland. Eventually the residual urine will flow by gravity and soil the underclothing or trousers. To prevent such delayed gravity flow, the man may forcefully shake the penis while over a urinal to discharge the residual urine. In the course of said shaking however, the path of the exiting urine is uncertain and may contact the hands, trousers, floor and wall. This situation is not only generally unsanitary, but could lead to the spread of contagious diseases such as AIDS. Although various devices and napkin-like products have earlier been proposed to cope with this problem, such earlier expedients have been either too expensive or impractical in terms of comfort and ease of use.

Accordingly, it is an object of the present invention to provide an improved sanitary napkin for male hygiene.

It is another object of this invention to provide a sanitary napkin adapted to envelop the male genital organ.

It is a further object of the present invention to provide a sanitary napkin of the aforesaid nature that is easily dispensed from a storage state and easily employed.

It is still another object of this invention to provide a sanitary napkin of the aforesaid nature of low cost and disposable in a toilet bowl.

These objects and other objects and advantages of the invention will be apparent from the following description.

SUMMARY OF THE INVENTION

The above and other beneficial objects and advantages are accomplished in accordance with the present invention by a napkin of thin water-absorbent dissolving-type paper amenable to storage as a multitude of napkins in a stack or roll or in nested relationship, said napkins being capable of existing in either an open state or in a functional state, the open state being easily converted into the functional state by the user, said functional state having an enclosure region having a closed tip extremity and open base extremity, and two opposed elongated strips in facing disposition emergent from said tip extremity.

In preferred specific embodiments, the napkin may be an integral piece of flat paper pre-folded and storable in a stacked package form for easy dispensing. In other embodiments, the elongated strips of the napkin may be contoured so that in their facing disposition they define an enclosure region adapted to embrace the shaft portion of the penis. The opposed elongated strips may be bridged by folded pleats. In still other embodiments, the napkin may be fabricated by the interadherence of two or more sheets of paper in a manner to define a generally conically-shaped enclosure region adapted to receive the head of the penis.

The term "dissolving-type paper" is intended to denote papers which easily disintegrate in water and can safely be disposed of in a toilet bowl in the usual manner of disposal of toilet tissue.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

DESCRIPTION OF THE PREFERRED EMBODIMENTS

Figure 1:
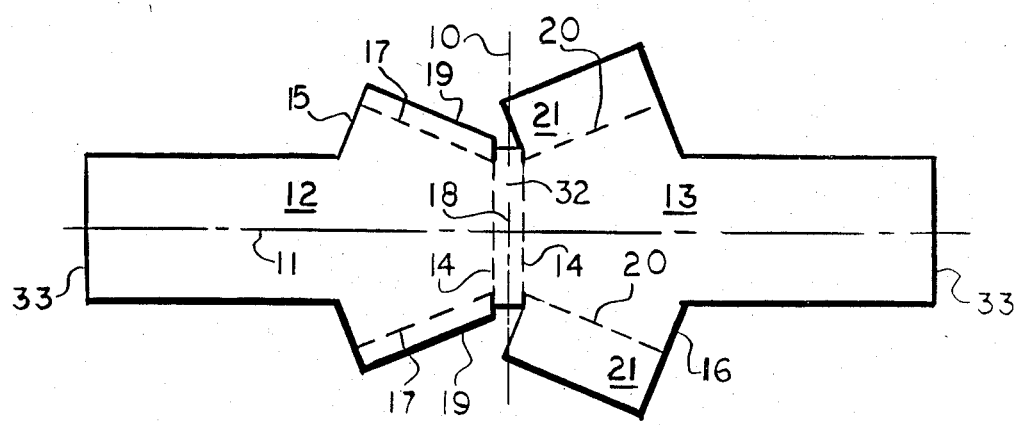
FIG. 1 is a plan view of an embodiment of the napkin of this invention in its open state.

Referring to FIG. 1, an embodiment of the napkin of this invention is shown in its open state as a substantially flat, integral piece of dissolving-type water-absorbent paper. The paper has substantially two axes of symmetry, namely a lateral axis 10, and a longitudinal axis 11 in perpendicular disposition to said lateral axis. The intersection of said axes defines a center point 18. The paper is shaped so as to have two elongated portions 12 and 13 in opposed relationship about axis 10, and adapted to fold upon each other about fold lines 14 so as to be in facing relationship with distal extremities 33 disposed one above the other. The separation of fold lines 14 is preferably between about $\frac{1}{4}"$ and $\frac{1}{2}"$, thereby forming a spacer zone 32 which causes the joined or proximal extremities of said elongated portions to be held slightly out of contacting abutment when the elongated portions are folded upon each other.

Widened portions 15 and 16 are associated with the joined extremities of elongated portions 12 and 13, respectively. Fold lines 17 are disposed within widened portion 15 symmetrically spaced about axis 11 and angled generally toward center point 18. The fold lines 17 define flaps 19 adapted to be folded inwardly toward axis 11.

In similar manner, fold lines 20 are disposed within widened portion 16 symmetrically spaced about axis 11 and angled generally toward center point 18. Fold lines 20 define flaps 21 adapted to be folded inwardly toward axis 11. The width of flaps 19 are shown to be smaller than the width of flaps 21. The center region of each elongated portion 12 and 13 may be flat, or may be concavely contoured below the plane of the remainder of the paper. The contour may be in the nature of a circular cylindric surface.

Figure 2:
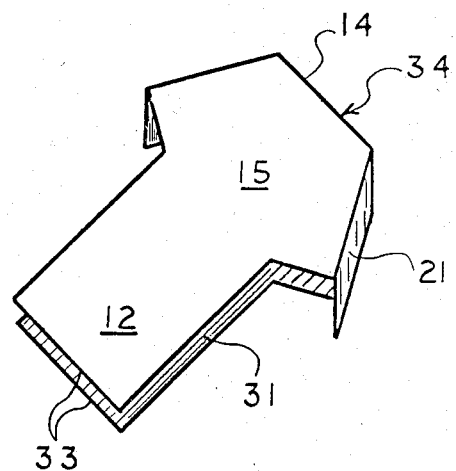
FIG. 2 is a perspective view of the napkin of FIG. 1 in its functional state.

When the paper of FIG. 1 is folded in a manner to bring elongated portions 12 and 13 into facing disposition, and the flaps are folded toward longitudinal axis 11, the structure shown in FIG. 2 is produced. It is seen that the facing elongated portions form a channel-like structure 31 into which the penis may be inserted, and the widened portions 15 and 16 interact with said flaps to form an enclosure 34 to accommodate the head of the penis.

By virtue of such manner of construction, the napkin may be easily removed from storage in a dispensing device, utilized for its intended purpose, and readily disposed of.

Figure 3:
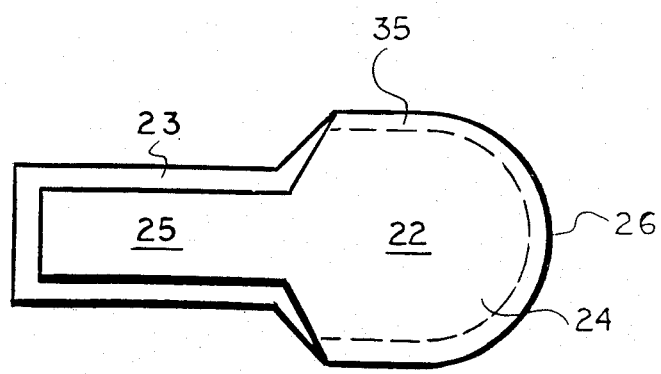
FIG. 3 is a plan view of a second embodiment of the napkin.

The embodiment of FIG. 3 represents a napkin fabricated by the interadhesion of shaped upper sheet 22 to shaped lower sheet 23. Each sheet is generally comprised of an enlarged forward extremity 24 and opposed elongated narrow portion 25. Interadhesion is achieved in a perimeter zone 35 at the forward edge 26 of the enlarged extremity.

By virtue of the construction of the napkin of FIG. 3, the forward extremity functions as an enclosure for the head of the penis, and the narrow portions 25 embrace the shaft of the penis.

Figure 4:
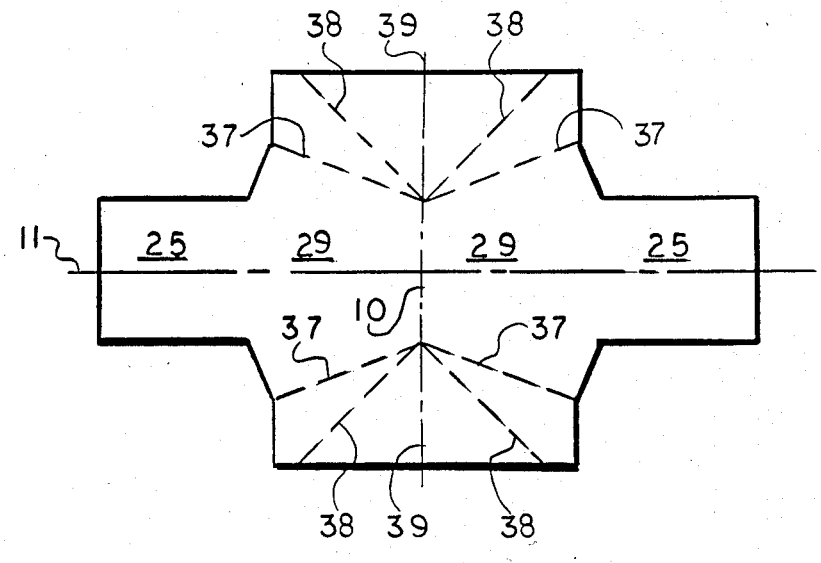
FIG. 4 is a plan view of a third embodiment of the napkin in its open state.

The embodiment of the napkin shown in FIG. 4 is comprised of a single flat piece of paper symmetrically contoured about longitudinal and lateral axes 11 and 10, respectively. When folded about lateral axis 11 so that elongated portions 25 are in facing relationship, and further folded along lines 37, 38 and 39 to form pleats, a configuration is produced wherein the enlarged central portions 29 form an enclosure bounded at both sides by said pleats. In folding the napkin of FIG. 4, fold lines 37 and 39 become interiorly directed edges, and fold line 38 becomes an outwardly directed edge.

Figure 5:
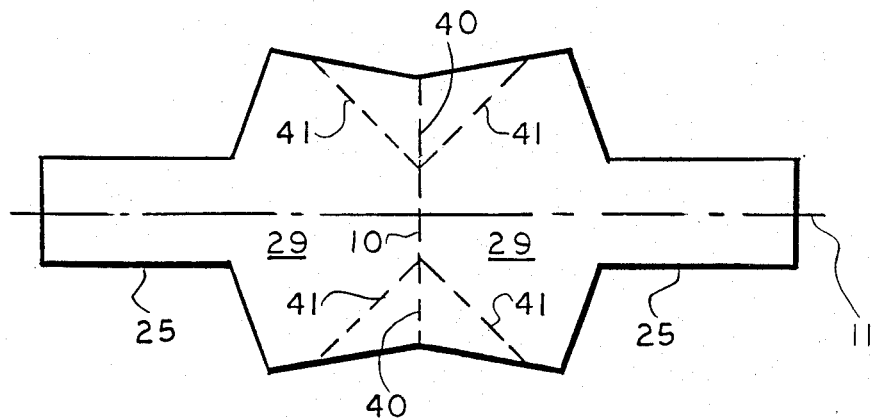
FIG. 5 is a plan view of a fourth embodiment of the napkin in its open state.
Figure 6:
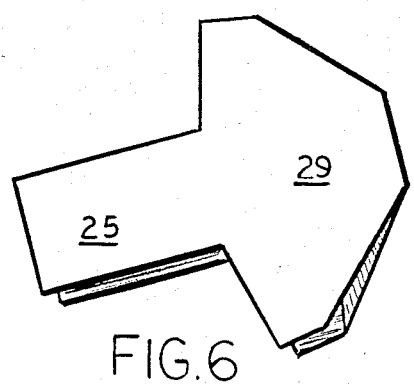
FIG. 6 is a perspective view of the embodiment of FIG. 5 in its functional state.

The embodiment of the napkin shown in FIGS. 5 and 6 is comprised of a single flat piece of paper symmetrically contoured about longitudinal and lateral axes 11 and 10, respectively. When folded about lateral axis 11 so that elongated portions 25 are in facing relationship, and further folded inwardly at lines 40 and outwardly at lines 41, the configuration of FIG. 6 is produced wherein the enlarged central portions 29 form an enclosure which accommodates the head of the penis. The pleats formed by the folding about lines 40 and 41 constitute side boundaries of the enclosure.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described our invention, what is claimed is:

1. A napkin of thin water-absorbent dissolving-type paper amenable to storage as a multitude of napkins in a stacked array for easy dispensing, said napkin comprised of an integral piece of pre-folded paper having a flat storage configuration and being deployable to a functional state by folding about a lateral axis, said functional state being characterized in having an enclosure region, two opposed elongated strips emergent from said enclosure region, and a side boundary.

2. The napkin of claim 1 wherein part of the side boundary of said enclosure is comprised of folded pleats.

* * * * *